United States Patent
Akporiaye et al.

[11] Patent Number: 5,817,596
[45] Date of Patent: Oct. 6, 1998

[54] CATALYST, AND PROCESSES FOR DEHYDROGENATING DEHYDROGENATABLE HYDROCARBONS

[75] Inventors: Duncan Akporiaye, Oslo; Morten Ronnekleiv; Preben Hasselgard, both of Trondheim, all of Norway

[73] Assignee: Den norske stats oljeselkap A.S., Stavanger, Norway

[21] Appl. No.: 569,185

[22] PCT Filed: Jun. 1, 1994

[86] PCT No.: PCT/NO94/00102

§ 371 Date: Dec. 14, 1995

§ 102(e) Date: Dec. 14, 1995

[87] PCT Pub. No.: WO94/29021

PCT Pub. Date: Dec. 22, 1994

[30] Foreign Application Priority Data

Jun. 14, 1993 [NO] Norway ..................................... 932173

[51] Int. Cl.⁶ ........................................................ B01J 23/62
[52] U.S. Cl. ......................... 502/327; 502/330; 502/339; 502/349; 502/352
[58] Field of Search ...................... 502/327, 330, 502/333, 334, 339, 344, 349, 352, 341

[56] References Cited

U.S. PATENT DOCUMENTS

| | | | |
|---|---|---|---|
| 3,670,044 | 6/1972 | Drehman et al. | 260/683.3 |
| 3,842,139 | 10/1974 | Kehl et al. | 260/683.3 |
| 4,169,815 | 10/1979 | Drehman | 252/466 PT |
| 4,451,683 | 5/1984 | Davies et al. | 570/224 |
| 4,788,371 | 11/1988 | Imai et al. | 585/443 |

FOREIGN PATENT DOCUMENTS

| | | | |
|---|---|---|---|
| 86201283 | 7/1986 | European Pat. Off. | B01J 23/74 |
| 0 253 924 | 1/1988 | European Pat. Off. | B01J 23/74 |
| 88312103 | 12/1988 | European Pat. Off. | C07C 5/48 |

*Primary Examiner*—Glenn Caldarola
*Assistant Examiner*—Alexander G. Ghyka
*Attorney, Agent, or Firm*—Kirkpatrick & Lockhart LLP

[57] ABSTRACT

A new catalyst, especially for the dehydrogenation of dehydrogenatable $C_{2-30}$ hydrocarbons. The catalyst comprises a carrier consisting essentially of a mixed oxide of magnesium and alumina Mg(Al)O, and also comprises a Group VIII noble metal, a Group IVA metal and optionally a Group IA alkali metal. The catalyst may be subjected to a pretreatment comprising a reduction, a subsequent oxidation and finally a second reduction. The catalyst is particularly suitable for the dehydrogenation of $C_{2-5}$ paraffins to olefins, with and without simultaneous oxidation of hydrogen.

18 Claims, No Drawings

CATALYST, AND PROCESSES FOR DEHYDROGENATING DEHYDROGENATABLE HYDROCARBONS

BACKGROUND OF THE INVENTION

Field of the Invention

The present invention relates to a new catalyst, a process for preparing the catalyst and processes for the dehydrogenation of dehydrogenatable $C_{2-30}$ hydrocarbons, preferably $C_{2-5}$ paraffins, using the new catalyst.

DESCRIPTION OF THE INVENTION BACKGROUND

The dehydrogenation of paraffins to olefins is of considerable commercial importance due to the need for olefins for the manufacture of products such as high octane gasolines, synthetic elastomers, detergents, plastics, ion exchange resins and pharmaceutical products. For a dehydrogenation process to be commercially useful, it must utilize catalysts exhibiting a high activity, a high rate of conversion, a high selectivity for the formation of olefins, and a high stability.

A large number of catalysts are previously known for the dehydrogenation of paraffins. These catalysts comprise a solid carrier material on an inorganic oxide basis and various catalytic metals and promoter metals deposited on the carrier material or incorporated into the carrier material by other means. Carrier materials on an alumina basis have been widely used in such dehydrogenation catalysts.

U.S. Pat. No. 4,788,371 discloses such catalyst and a process for the steam dehydrogenation of dehydrogenatable hydrocarbons with oxidative reheating. A dehydrogenatable $C_{2-30}$ hydrocarbon, steam and an oxygen-containing gas are contacted in a reaction zone with a catalyst comprising a Group VIII noble metal, one or more components selected from lithium, potassium, rubidium, cesium and francium, and a component selected from boron, gallium, indium, germanium, tin and lead, deposited on an inorganic oxide carrier material. The preferred carrier material is alumina having a surface area of 1–500 $m^2/g$, preferably 5–120 $m^2/g$. Alumina is employed as the catalyst carrier in all the working examples of the patent. A preferred catalyst according to said U.S. patent contains about 0.70 wt. % of platinum, about 0.50 wt. % of tin and about 3.86 wt. % of cesium, and has a surface area of about 85 $m^2/g$.

Mixtures of magnesium oxide MgO and alumina $Al_2O_3$ and mixed oxides of Mg and Al have also been utilized as catalysts, and as carrier materials for catalysts. International Patent Application No. PCT/JP89/00053 discloses an alkoxylation catalyst comprising a magnesium oxide that has been modified by adding thereto at least one trivalent metal ion, preferably selected from $Al^{3+}$ and $Ga^{3+}$. British Patent Application GB 2,225,731 discloses a catalyst for hydrotreatment, e.g. hydrodemetallization or hydrodesulphurization, comprising in a substantially homogenous phase magnesia and alumina wherein the molar ratio of Mg to Al is preferably from 3:1 to 10:1, together with a Group VI metal and/or at least one Group VIII metal.

SUMMARY OF THE INVENTION

It has now been found that if a mixed oxide of Mg and Al is used in combination with a Group VIII noble metal and certain promoters of the kind disclosed in the above-mentioned U.S. Pat. No. 4,788,371, a catalyst can be obtained which exhibits improved activity and stability when used for dehydrogenating dehydrogenatable hydrocarbons.

Thus, the invention provides a catalyst comprising a combination of a carrier, constituted essentially by a mixed oxide of magnesium and aluminum Mg(Al)O, a Group VIII noble metal, a Group IVA metal, and optionally a Group IA alkali metal.

Preferably, the catalyst has been subjected to a pretreatment comprising a reduction, preferably in hydrogen, a subsequent oxidation, preferably in air optionally mixed with nitrogen, and finally a second reduction, preferably in hydrogen (ROR pretreatment; ROR=Reduction-Oxidation-Reduction).

The Group VIII noble metal is preferably selected from platinum and palladium, with platinum being the most preferred. The Group IVA metal is preferably selected from tin and germanium, with the most preferred metal being tin.

It has further been shown that the selectivity of the new catalysts in a dehydrogenation process is further improved by including therein a Group IA alkali metal, preferably cesium or potassium, most preferably cesium.

It is remarkable that the new catalyst exhibits a very high activity in the dehydrogenation of hydrocarbons even with a low content of Group VIII noble metal of e.g. 0.2–0.4 wt. %.

The Group VIII metal, the Group IVA metal and the optional Group IA metal can be incorporated into the carrier by any of the methods known in the art. A preferred method consists in impregnating the oxide carrier with solutions or suspensions of decomposable compounds of the metals to be incorporated.

The catalyst and its preparation is described in more detail below with reference to embodiments wherein platinum, tin and optionally cesium are deposited on the carrier material, but the description is also valid for the deposition of other metals within the scope of the invention, with any adaptations that will be obvious to a person skilled in the art.

DETAILED DESCRIPTION OF THE PREFERRED EMBODIMENTS

The mixed oxide of magnesium and aluminum, Mg(Al)O, which is utilized as a carrier material in the catalyst of the invention, can be prepared by adding a solution of sodium hydroxide and sodium carbonate to a solution of magnesium nitrate and aluminum nitrate according to the method described in Journal of Catalysis 94 (1985), pp. 547–557. Instead of sodium hydroxide and sodium carbonate, potassium hydroxide and potassium carbonate can be used, see Applied Catalysis 54 (1989) pp. 79–90. By evaporation (drying) of the above mentioned mixtures the compound hydrotalcite, $Mg_6Al_2(OH)_{16}CO_3 4H_2O$, is formed, which compound is calcined at 5000° to 800° C. to give Mg(Al)O. It is preferred, however, to modify this process somewhat by using ammonium hydroxide and ammonium carbonate instead of the respective compounds sodium hydroxide/potassium hydroxide and sodium carbonate/potassium carbonate, whereby a larger and more stable surface area is obtained. The obtained Mg(Al)O is characterized by a magnesia structure wherein some of the magnesium atoms are replaced by aluminum atoms. The molar ratio of Mg to Al is typically ranging from 1:1 to 10:1, and the surface area is typically ranging from 100 to 300 $m^2/g$, preferably from 140 to 210 $m^2/g$. The particle size can be in the range of 100 pm to 20 mm.

The deposition of platinum and tin on the Mg(Al)O carrier material can advantageously be carried out in one step, e.g. by using tin chloride and hexachloroplatinic acid dissolved in ethanol. A method for depositing platinum and tin in a single step is described in J. Catalysis, Vol. 128, 1991, page 1. By carrying out a simultaneous deposition of platinum and tin on the Mg(Al)O material, the number of required calcination steps is reduced, which makes it easier to obtain a high surface area of the Mg(Al)O material. Other suitable impregnation procedures are described in the above-mentioned U.S. Pat. No. 4,788,371, in U.S. Pat. No. 4,962,265 and in EP 0,098,622.

In cases where the catalyst shall contain cesium, a deposition of cesium can be effected in a separate step, after the deposition of tin and platinum and the subsequent calcination, using cesium nitrate dissolved in water. The impregnation with cesium nitrate can be carried out as described in U.S. Pat. No. 4,788,371.

The ROR pretreatment of the catalyst is conveniently effected by carrying out a reduction of the catalyst in hydrogen, a subsequent oxidation in air optionally mixed with nitrogen, and finally a second reduction in hydrogen. The pretreatment can be carried out at temperatures in the range of 500° to 700° C. and by using space velocities (GHSV) for the treatment gases of 10 to 100,000N ml $g^{-1}$ $h^{-1}$, preferably 100 to 5000N ml $g^{-1}$ $h^{-1}$. The initial reduction of the catalyst with hydrogen is carried out for a period of 1 minute to 10 hours, usually for about 2 hours. The subsequent oxidation of the reduced catalyst in air optionally mixed with nitrogen is carried out for a period of 1 minute to 10 hours, usually for about 2 hours. The oxidation may advantageously be accomplished by first treating the catalyst for about 1 hour in a stream of nitrogen containing about 20% by volume of air, and then treating it for about 1 hour in pure air. The final reduction with hydrogen is carried out under similar conditions as the initial reduction.

Thus, the invention also relates to a process for preparing the above-described ROR pretreated catalyst. The process is characterized by the steps of incorporating a Group VIII noble metal, a Group IVA metal and optionally a Group IA alkali metal into a carrier consisting essentially of a mixed oxide of magnesium and aluminum Mg(Al)O, and subjecting the material thus obtained to a pretreatment (ROR pretreatment) comprising a reduction, preferably in hydrogen, a subsequent oxidation, preferably in air optionally mixed with nitrogen, and finally a second reduction, preferably in hydrogen.

The invention further provides a process for dehydrogenating dehydrogenatable $C_{2-C30}$ hydrocarbons, preferably $C_{2-C5}$ paraffins, comprising contacting the hydrocarbons, under suitable dehydrogenation conditions in one or more reaction zones, with a solid catalyst comprising a combination of a carrier, constituted essentially by a mixed oxide of magnesium and aluminum Mg(Al)O, a Group VIII noble metal, a Group IVA metal and optionally a Group IA alkali metal.

In accordance with usual practice in the dehydrogenation of hydrocarbons, the hydrocarbons are preferably contacted with the solid catalyst in a gaseous phase, mixed with usual additives such as steam, nitrogen and hydrogen. The feed mixture containing the hydrocarbons is preferably introduced into a reactor having one or more fixed catalyst beds, and the dehydrogenation is preferably carried out at a temperature ranging from 500° to 700° C., at a pressure ranging from 0.5 to 1.5 bars absolute, and using a space velocity (GHSV) ranging from 10 to 10.000N ml $g^{-1}$ $h^{-1}$.

The new catalyst has also been shown to be very suitable in cases where the dehydrogenation of hydrocarbons is carried out in combination with admixing of oxygen and combustion of hydrogen, because the new catalyst also exhibits a selective catalytic effect on the oxidation of hydrogen to water.

It is well known in the art of dehydrogenating dehydrogenatable hydrocarbons that it is advantageous to oxidize with an oxygen-containing gas the hydrogen formed in the reaction. Because the dehydrogenation process is endothermic, oxidation of the formed hydrogen can be utilized to maintain the desired reaction temperature during the dehydrogenation. For such heating purpose it will often be advantageous even to add a supplementary amount of recirculated hydrogen to the reaction mixture. In addition to achieving a desired heat balance, the lowering of the hydrogen concentration in the reaction mixture resulting from the combustion will shift the equilibrium of the desired dehydrogenation reactions in the direction of higher yields of unsaturated hydrocarbons. Although it will be advantageous for that reason to achieve a high hydrogen conversion, it is important however to avoid excessive concurrent oxidation of hydrocarbons, which would reduce the total yield of the process. It is therefore important to achieve a maximum of selectivity of the oxidation of the hydrogen formed in the dehydrogenation process. It has been found that such selective oxidation is achieved with the new catalyst.

Thus, the invention also provides a process for dehydrogenating dehydrogenatable $C_{2-C30}$ hydrocarbons, preferably $C_{2-C5}$ paraffins, in combination with admixing of an oxygen-containing gas, preferably oxygen, and combustion of hydrogen, comprising contacting the hydrocarbons under suitable dehydrogenation conditions in one or more reaction zones, with a solid catalyst comprising a combination of a carrier, constituted essentially by a mixed oxide of magnesium and aluminum Mg(Al)O, a Group VIII noble metal, a Group IVA metal and optionally a Group IA alkali metal.

In accordance with usual practice in such dehydrogenation of hydrocarbons, the hydrocarbons are contacted with the solid catalyst in a gaseous phase, mixed with an oxygen-containing gas and with usual additives such as steam, any supplementary quantities of hydrogen, and nitrogen. The feed mixture containing the hydrocarbons is preferably introduced into a reactor having one or more fixed catalyst beds, with oxygen-containing gas being introduced and admixed with the feed stream even between the catalyst beds when more than one such bed is used. The dehydrogenation is preferably carried out at a temperature ranging from 400° to 700° C., at a pressure ranging from 0.5 to 3 bars absolute, and using a space velocity (GHSV) ranging from 10 to 10.000N ml $g^{-1}$ $h^{-1}$.

In both of the two types of the dehydrogenation process the activity of the catalyst will decrease with time. When the activity has become undesirably low, the catalyst may be regenerated, e.g. in the same reactor. The regeneration can be carried out by burning off the coke that has been formed on the catalyst, with an oxygen-containing gas for a period of time ranging from 1 minute to 10 hours, preferably in a stream of air optionally mixed with nitrogen. The catalyst is then subjected to a reduction treatment for a period of 1 minute to 10 hours in a stream of hydrogen. Said treatments are suitably carried out at 300° to 700° C. using a space velocity (GHSV) for the treatment streams of 10 to 10,000N ml $g^{-1}$ $h^{-1}$, preferably 100 to 5000N ml $g^{-1}$ $h^{-1}$. If desired, a redispersion of the noble metal, e.g. platinum, in the catalyst can be effected using a chlorine-containing gas after the burning off of the coke but prior to the reduction treatment.

The regeneration of the catalyst restores to a substantial extent the original characteristics of the catalyst. The restoration of the activity and the selectivity of the catalyst will be more complete in the temperature range of 300° C. to 400° C. than at the higher temperatures. Admixing nitrogen with the air stream utilized for the oxidation also tends to improve the restoration of the properties of the catalyst.

Compared to the previously known dehydrogenation catalysts on an alumina basis, the new catalyst exhibits improved activity and improved stability.

The following examples illustrate the invention.

EXAMPLE 1

A Mg(Al)O material having an atomic ratio of Mg to Al of 2:1 to 3:1 was prepared according to the following procedure: An aqueous solution of 1.13 moles of NaOH and 0.045 mole of $Na_2CO_3$ was treated with a solution of 0.91 mole of $Mg(NO_3)_2 6H_2O$ and 0.09 mole of $Al(NO_3)_3 9H_2O$ at about 75° C. (pH=9.5). After filtration, washing and drying at about 100° C. for about 15 hours, a hydrotalcite $Mg_6Al_2(OH)_{16}CO_3 4H_2O$ was formed. The structure was confirmed by X-ray diffraction analysis. The material thus obtained was calcined at 700° C. for about 15 hours, whereby Mg(Al)O was formed. The structure was confirmed by X-ray diffraction analysis, and the surface area was measured to be 156 $m^2/g$.

EXAMPLE 2

A Mg(Al)O material having an atomic ratio of Mg to Al of 2:1 to 3:1 was prepared according to the following procedure: An aqueous solution of 1.13 moles of $NH_4OH$ and 0.045 mole of $(NH_4)_2CO_3$ was treated with a solution of 0.91 mole of $Mg(NO_3)_2 6H_2O$ and 0.09 mole of $Al(NO_3)_3 9H_2O$ at a temperature of about 75° C. (pH=9.5). After filtration, washing and drying at about 100° C. for about 15 hours, a hydrotalcite $Mg_6Al_2(OH)_{16}CO_3 4H_2O$ was formed. The material thus obtained was calcined at 700° C. for about 15 hours, whereby Mg(Al)O was formed. The structure was confirmed by X-ray diffraction analysis, and the surface area was measured to be 198 $m^2/g$.

EXAMPLE 3

A Mg(Al)O material having a particle size of 300–400 $\mu$m, prepared according to Example 1, was impregnated with a solution containing tin chloride and hexachloroplatinic acid and with a solution of cesium nitrate, according to the following procedure:

0.1150 g $SnCl_2 2H_2O$ and 0.0805 g $H_2PtCl_6 6H_2O$ were dissolved in 60 ml of ethanol and the mixture was added to 10.1 g of Mg(Al)O. After completion of the impregnation the material thus obtained was evaporated to dryness in a vacuum and was then dried at about 100° C. for about 15 hours, whereupon the dried material was calcined at 560° C. for about 3 hours in air supplied in an amount of 100 $cm^3/min$.

0.0711 g $CsNO_3$ dissolved in 25 ml of water was then added to the calcined material. Upon completion of the impregnation, the material thus obtained was dried at about 100° C. for about 15 hours. The dried material was calcined at 560° C. for about 3 hours in air supplied in an amount of 100 $cm^3/min$.

3 g of the calcined product were then reduced at 600° C. for 2 hours in a stream of $N_2$ supplied in an amount of 20 $cm^3/min$.

The reduced product was then oxidized at 600° C. for about 1 hour in a stream of $N_2$ containing 20% by volume of air, added in an amount of 50 $cm^3/min$, and for about 1 hour in pure air supplied in an amount of 50 $cm^3/min$. The oxidized product was then reduced in the same manner as before the oxidation.

A catalyst was obtained which had the following chemical composition:

0.3 wt. % Pt
0.6 wt. % Sn
0.5 wt. % Cs
98.6 wt. % Mg(Al)O.

The catalyst was tested for a dehydrogenation of propane in a microreactor equipped with a fixed catalyst bed, at the following conditions:

| Dehydrogenation temperature: | 600° C. |
|---|---|
| Dehydrogenation pressure: | 1 bar abs. |
| Space velocity (GHSV): | 2100 N ml $g^{-1}$ $h^{-1}$ |
| Amount of catalyst: | 3.0 g |
| Composition of the feed stream: | |
| Propane | 35 Nml/min |
| Hydrogen | 5 Nml/min |
| Nitrogen | 25 Nml/min |
| Steam | 41 Nml/min |

The results thereby obtained are given in Table 1.

EXAMPLE 4

Comparison Example

The procedure of Example 3 was repeated, with the following exception: After the first reduction of the calcined product with $H_2$, the oxidation in air-containing $N_2$ and the subsequent second reduction with $H_2$ were omitted.

The catalyst was used for a dehydrogenation of propane under the same conditions as in Example 3. The results obtained are given in Table 1.

EXAMPLE 5

The procedure of Example 3 was followed, including the post-treatment consisting in a reduction, a subsequent oxidation, and a second reduction (ROR pretreatment) of the calcined catalyst, but the impregnation with $CsNO_3$ for incorporation of cesium was omitted. The impregnation with a solution containing tin chloride and hexachloroplatinic acid was accomplished in the presence of quantities of tin chloride and hexachloroplatinic acid resulting in a catalyst having the chemical composition:

0.3 wt. % Pt
0.6 wt. % Sn
99.1 wt. % Mg(Al)O.

The catalyst was used for a dehydrogenation of propane under the same conditions as in Example 3. The results obtained are given in Table 1.

EXAMPLE 6

A Mg(Al)O material having a particle size of 300–400 $\mu$m, prepared according to Example 2, was impregnated with a solution containing tin chloride and hexachloroplatinic acid according to the following procedure:

0.1150 g $SnCl_2 2H_2O$ and 0.0805 g $H_2PtCl_6 6H_2O$ were dissolved in 60 ml of ethanol and the mixture was added to 10.1 g of Mg(Al)O After completion of the impregnation the material thus obtained was evaporated to dryness in a vacuum and then dried at about 100° C. for about 15 hours, whereupon the dried material was calcined at 560° C. for about 3 hours in air supplied in an amount of 100 $cm^3/min$.

3 g of the calcined product were then reduced at 600° C. for 2 hours in a stream of $H_2$ supplied in an amount of 20 $cm^3/min$.

The reduced product was thereafter oxidized at 600° C. for about 1 hour in a stream of $N_2$ containing 20% by volume of air, supplied in an amount of 50 cm³/min, and for about 1 hour in pure air supplied in an amount of 50 cm³/min. The oxidized product was then reduced in the same manner as before the oxidation.

A catalyst was obtained which had the following chemical composition:
0.3 wt. % Pt
0.6 wt. % Sn
99.1 wt. % Mg(Al)O.

The catalyst was used for a dehydrogenation of propane under the same conditions as in Example 3. The results obtained are given in Table 1.

EXAMPLE 7

The procedure of Example 6 was followed, including the post-treatment consisting in a reduction, a subsequent oxidation, and a second reduction (ROR pretreatment) of the calcined catalyst, but the impregnation with a solution containing tin chloride and hexachloroplatinic acid was accomplished in the presence of quantities of tin chloride and hexachloroplatinum acid resulting in a catalyst having the chemical composition:
0.3 wt. % Pt
0.9 wt. % Sn
98.8 wt. % Mg(Al)O.

The catalyst was used in dehydrogenation of propane under the same conditions as in Example 3. The results obtained are given in Table 1.

EXAMPLE 8

The procedure of Example 6 was followed, including the post-treatment consisting in a reduction, a subsequent oxidation, and a second reduction (ROR pretreatment) of the calcined catalyst, but the impregnation with a solution containing tin chloride and hexachloroplatinic acid was accomplished in the presence of such quantities of tin chloride and hexachloroplatinum acid that a catalyst was obtained having the chemical composition:
0.3 wt. % Pt
1.2 wt. % Sn
98.5 wt. % Mg(Al)O.

The catalyst was used for a dehydrogenation of propane under the same conditions as in Example 3. The results obtained are given in Table 1.

EXAMPLE 9

Comparison Example

A known dehydrogenation catalyst was prepared according to the process disclosed in U.S. Pat. No. 4,788,371. 0.179 g of $SnCl_2 2H_2O$ dissolved in 14 ml of water was added to 18.8 g of θ-alumina having a particle size of 100 to 400 μm. After completion of the impregnation, the resulting material was dried at about 100° C. for about 6 hours. The dried material was calcined for about 3 hours at 600° C. in a stream of air supplied in an amount of 100 cm³/min.

0.349 g of $H_2PtCl_6 6H_2O$ dissolved in 14 ml of water was added to the calcined material. After completion of the impregnation, the resulting material was dried at about 100° C. for about 15 hours. The dried material was calcined for a period of 3 hours at 570° C. in a stream of air containing 10% of steam and supplied in an amount of about 100 cm³/min.

1.06 g of $CsNO_3$ dissolved in 14 ml of water were added to the calcined material. Upon completion of the impregnation, the resulting material was dried at about 100° C. for about 30 hours. The dried material was calcined for about 3 hours at 570° C. in an air stream supplied in an amount of about 100 cm³/min.

3 g of the obtained catalyst were then reduced at 600° C. for about 2 hours in a stream of $H_2$ supplied in an amount of 20 cm³/min.

A catalyst was obtained having the chemical composition:
0.7 wt. % Pt
0.5 wt. % Sn
3.9 wt. % Cs
94.9 wt. % θ-alumina.

The catalyst was used for a dehydrogenation of propane under the same conditions as in Example 3. The results obtained are given in Table 1.

EXAMPLE 10

Comparison Example

A catalyst was prepared according to Example 9, whereupon 3 g of the reduced catalyst were oxidized at 600° C. for about 1 hour in a stream of $N_2$ containing 20% by volume of air, supplied in an amount of 50 cm³/min, and for about 1 hour in pure air supplied in an amount of 50 cm³/min. The oxidized product was then reduced in the same manner as before the oxidation, i.e. at 600° C. for a period of 2 hours in a stream of $H_2$ supplied in an amount of 20 cm³/min.

Thus, the post-treatment of the catalyst accomplished after the calcination corresponded to a ROR pretreatment as prescribed for the catalysts of the invention.

The catalyst was used for a dehydrogenation of propane under the same conditions as in Example 3. The results obtained are given in Table 1.

TABLE 1

| | | | Dehydrogentation of propane to propene. | | | | |
|---|---|---|---|---|---|---|---|
| Example | Carrier | Metal content (wt. %) | Conv. of propane 5 h (%) | Conv. of propane 25 h (%) | C-sel. to propene 5 h (%) | C-sel. to propene 25 h (%) | Yield of propene[5] 25 h (%) |
| 3 | Mg(Al)O | 0.3 Pt 0.6 Sn 0.5 Cs | 52.8 | 45.6 | 97.5 | 97.8 | 44.6 |
| 4[1] Comp. cat. | " | 0.3 Pt 0.6 Sn 0.5 Cs | 19.3 | 16.7 | 97.8 | 97.3 | 16.2 |

TABLE 1-continued

Dehydrogentation of propane to propene.

| Example | Carrier | Metal content (wt. %) | Conv. of propane 5 h (%) | Conv. of propane 25 h (%) | C-sel. to propene 5 h (%) | C-sel. to propene 25 h (%) | Yield of propene[5] 25 h (%) |
|---|---|---|---|---|---|---|---|
| 5 | " | 0.3 Pt 0.6 Sn | 58.7 | 53.0 | 93.3 | 97.3 | 51.6 |
| 6[2] | " | 0.3 Pt 0.6 Sn | 58.8 | 57.5 | 93.0 | 95.9 | 55.1 |
| 7[2] | " | 0.3 Pt 0.9 Sn | 58.0 | 57.8 | 93.9 | 96.1 | 55.5 |
| 8[2] | " | 0.3 Pt 1.2 Sn | 58.6 | 57.5 | 94.9 | 95.9 | 55.1 |
| 9[3] Comp. cat. | θ-Al$_2$O$_3$ | 0.7 Pt 0.5 Sn 3.9 Cs | 38.0 | 27.0 | 97.0 | 95.0 | 25.7 |
| 10[4] Comp. cat. | θ-Al$_2$O$_3$ | 0.7 Pt 0.5 Sn 3.9 Cs | 41.4 | 31.0 | 96.4 | 95.9 | 29.7 |

[1]Without ROR pretreatment.
[2]Mg(Al)O having a large surface area (198 m$^2$/g).
[3]A catalyst known from U.S. Pat. 4,788,371.
[4]A catalyst known from U.S. Pat. 4,788,371, but subjected to a ROR pretreatment.

[5]Yield of propene = $\dfrac{\text{Number of moles of C as C}_3\text{H}_6}{\text{Number of moles of C as C}_3\text{H}_8 + \text{Number of moles of C in products}}$ The results in Table 1 show that a ROR pretreated catalyst of the invention provides a large increase in the propane conversion compared to a similar catalyst not having been subjected to such pretreatment (Example 3 compared to Example 4). The selectivity for forming propene is retained at about the same level, whereby the total yield of propene is substantially increased.

The results in Table 1 also show that an increase in the surface area of the Mg(Al)O material from 156 m$^2$/g to 198 m$^2$/g results in a somewhat more stable catalyst and consequently in an increased yield of propene after 25 hours (Example 6 compared to Example 5).

An increase of the catalysts' content of Sn from 0.6 wt. % to 0.9 wt. % appears to result in a further increased yield of propene (Example 7 compared to Example 6).

The previously known catalyst of Example 9 gives a substantially lower yield of propene than the new catalysts (Examples 3, 5, 6, 7, 8). When the previously known catalyst of Example 9 is subjected to a complete ROR pretreatment as prescribed according to the invention (Example 10), the yield is improved even for said previously known catalyst. Nonetheless, the improving effect of the ROR pretreatment is not nearly as good for the known catalyst as for the new catalysts. Thus, the new catalysts also give a substantially better yield of propene than the ROR pretreated catalyst of Example 10.

EXAMPLE 11

The performance of one of the new catalysts of the invention was compared to the performance of a previously known catalyst for a dehydrogenation of propane accomplished in combination with combustion of hydrogen with an oxygen-containing gas. The combination of dehydrogenation and hydrogen combustion was carried out in a reactor comprising two catalyst zones and an intermediary oxygen admixing zone.

In addition to oxygen being added to the feed to the first catalyst zone, oxygen was also introduced into said oxygen admixing zone between said two catalyst zones.

The new catalyst (I) consisted of 0.3 wt. % Pt and 1.2 wt. % Sn on Mg(Al)O and was a catalyst similar to the one of Example 8 above, except that it had been prepared with a particle size of 1–2 mm.

The known catalyst (II) was a catalyst according to U.S. Pat. No. 4,788,371, consisting of 0.65 wt. % Pt, 1.15 wt. % Sn and 2.18 wt. % Cs on θ-alumina. Catalyst (II) had been prepared according to said U.S. Pat. No. 4,788,371, as described in Example 9 above, except that similarly with the new catalyst (I) it had been prepared with a particle size of 1–2 mm.

The conditions employed in the combined dehydrogenation and hydrogen combustion, and the results obtained, are summarized in the following Table 2.

TABLE 2

Dehydrogenation of propane to propene, with combustion of hydrogen.

| | Cat. II[(1)] | Cat. I[(2)] |
|---|---|---|
| Amount of catalyst | | |
| Total (g) | 119.3 | 77.6 |
| Step 1 (g) | 29.8 | 19.1 |
| Step 2 (g) | 89.5 | 58.5 |
| Main stream | | |
| C$_3$H$_8$ (N ml/min) | 1000 | 1000 |
| H$_2$ (N ml/min) | 400 | 400 |
| N$_2$ (N ml/min) | 45 | 45 |
| O$_2$ (N ml/min) | 130 | 130 |
| H$_2$O (N ml/min) | 1040 | 1040 |
| Admixed stream | | |
| O$_2$ (N ml/min) | 130 | 130 |
| N$_2$ (N ml/min) | 45 | 45 |
| Other conditions | | |
| Dehydrogen. temp. (°C.) | 600 | 600 |
| (GHSV) (N ml g$^{-1}$ h$^{-1}$) | 1400 | 2100 |
| Results | | |

TABLE 2-continued

Dehydrogenation of propane to propene, with combustion of hydrogen.

|  | Cat. II[1] | Cat. I[2] |
|---|---|---|
| Conv. of $C_3H_8$ (5 h) (%) | 45 | 57 |
| C-sel. to $C_3H_6$ (5 h) (%) | 94 | 90 |
| Conv. of $C_3H_8$ (20 h) (%) | 30 | 55 |
| C-sel. to $C_3H_6$ (20 h) (%) | 95 | 94 |
| Yield of $C_3H_6$ (20 h) (%) | 28.5 | 51.7 |
| Conv. of $O_2$ (5 h) (%) | 100 | 100 |
| O-sel. to ($H_2O$) (5 h) (%) | 88 | 80 |
| Conv. of $O_2$ (20 h) (%) | 100 | 100 |
| O-sel. to $H_2O$ (20 h) (%) | 95 | 87 |

[1]A catalyst according to U.S. Pat. No. 4,788,371, containing 0.65 wt. % Pt, 1.15 wt. % Sn and 2.18 wt. % Cs on (θ)-$Al_2O_3$.
[2]A new catalyst, containing 0.3 wt. % Pt and 1.2 wt. % Sn on Mg(Al)O.

The results in Table 2 show that the new catalyst I and the known catalyst II, which are both described in Example 11, are both capable of achieving a selective oxidation of the hydrogen in the gas mixture.

The conversion of propane $C_3H_8$, and thus the yield of propene $C_3H_6$, is substantially higher for the new catalyst than for the known catalyst, viz. 57% versus 45% after 5 hours, and 55% versus 30% after 20 hours of operation, respectively. The higher propene yield was achieved in spite of the fact that the gas space velocity per gram of catalyst and per hour (GHSV) was higher for the new catalyst (2100N ml $g^{-1}$ $h^{-1}$ versus 1400N ml $g^{-1}$ $h^{-1}$ for the known catalyst), and in spite of the fact that the content of active noble metal (platinum) was substantially lower in the new catalyst (0.3 wt. % versus 0.65 wt. % in the known catalyst). The higher (GHSV) used with the new catalyst was due to the fact that this catalyst had a lower bulk weight than the known catalyst. As a consequence of the lower bulk weight of the new catalyst, the advantage resulting from its low content of platinum was even more important than suggested by the percentual content alone. A low content of platinum in a commercial catalyst is important from an economical point of view.

The selectivity for oxidation of hydrogen to water is somewhat higher for the known catalyst than for the new catalyst, viz. 88% versus 80% after 5 hours, and 95% versus 87% after 20 hours of operation, respectively. This may be explained at least partly by the fact that the lower propane conversion achieved by the known catalyst resulted in the formation of lesser amounts of the desired dehydrogenated product, propene. Thus, with the known catalyst the oxidation of hydrogen to water was less burdened by competing oxidation of propene to carbon oxides.

We claim:

1. A catalyst comprising a combination of:
   a carrier comprising a mixed oxide of magnesium and aluminum Mg(Al)O having a magnesium oxide structure in which $Al^{3+}$ cations have replaced part of the $Mg^{2+}$ cations, in which oxide the molar ratio of magnesium to aluminum ranges from 1:1 to 10:1;
   a Group VIII noble metal;
   a Group IVA metal; and
   optionally a Group IA alkali metal.

2. The catalyst according to claim 1 wherein the molar ratio of magnesium to aluminum in the Mg(Al)O carrier ranges from 2:1 to 5:1.

3. The catalyst according to claim 1 wherein the surface area of the Mg(Al)O carrier is from 10 to 400 $m^2/g$.

4. The catalyst according to claim 1 wherein the surface area of the Mg(Al)O carrier is from 100 to 300 $m^2/g$.

5. The catalyst according to claim 1 wherein the surface area of the Mg(Al)O carrier is from 140 to 210 $m^2/g$.

6. The catalyst according to claim 1 wherein the catalyst contains:

0.05–5.0 wt. % Group VIII noble metal,
   0.05–7.0 wt. % Group IVA metal,
   0–5.0 wt. % Group IA metal,
   calculated on the total weight of the catalyst.

7. The catalyst according to claim 6 wherein the catalyst contains 0.1–1.0 wt. % of Group IA metal.

8. The catalyst according to claim 6 wherein the catalyst contains:

0.1–1.0 wt. % Group VIII noble metal,
   0.1–3.0 wt. % Group IVA metal,
   0–0.7 wt. % Group IA metal,
   calculated on the total weight of the catalyst.

9. The catalyst according to claim 8 wherein the catalyst contains 0.3–0.7 wt. % of Group IA metal.

10. The catalyst according to claim 8 wherein the catalyst contains:

0.2–0.4 wt. % Group VIII noble metal,
    0.3–1.5 wt. % Group IVA metal,
    0–0.6 wt. % Group IA metal,
    calculated on the total weight of the catalyst.

11. The catalyst according to claim 10 wherein the catalyst contains 0.4–0.6 wt. % of Group 1A metal.

12. The catalyst according to claim 1 wherein the Group IVA metal is tin or germanium.

13. The catalyst according to claim 1 wherein the Group VIII noble metal is platinum or palladium.

14. The catalyst according to claim 1 wherein the Group IA alkali metal is cesium or potassium.

15. A process for preparing a catalyst wherein the catalyst comprises a combination of a carrier comprised of a mixed oxide of magnesium and aluminum Mg(Al)O having generally a magnesium oxide structure in which $Al^{3+}$ cations have replaced part of the $Mg^{2+}$ cations, in which oxide the molar ratio of magnesium to aluminum ranges from 1:1 to 10:1; a Group VIII noble metal; a Group IVA metal; and optionally a Group IA alkali metal, the process comprising the steps of incorporating a Group VIII noble metal, a Group IVA metal and optionally a Group IA alkali metal into a carrier comprised of a mixed oxide of magnesium and aluminum Mg(Al)O, and subjecting the material thus obtained to a pretreatment comprising a reduction, a subsequent oxidation, and finally a second reduction.

16. The process according to claim 15 wherein the molar ratio of magnesium to aluminum in the Mg(Al)O carrier ranges from 2:1 to 5:1.

17. The process according to claim 15 wherein the reduction is in hydrogen, the oxidation is in air optionally mixed with nitrogen, and the second reduction is in hydrogen.

18. The process according to claim 15 wherein the pretreatment is carried out at temperatures of 500° to 700° C.

* * * * *

UNITED STATES PATENT AND TRADEMARK OFFICE
CERTIFICATE OF CORRECTION

PATENT NO. : 5,817,596
DATED : October 6, 1996
INVENTOR(S) : Akporiaye et al.

It is certified that error appears in the above-identified patent and that said Letters Patent is hereby corrected as shown below:

Title page,
In the Title, before "CATALYST" insert -- NEW --;

Column 2,
Line 50, delete "5000" and substitute therefor -- 500 --;
Line 62, delete "pm" and substitute therefor -- µm --;

Column 3,
Line 44, delete "$C_{2-c30}$" and substitute therefor -- $C_{2-30}$ --;
Line 45, delete "$C_{2-c5}$" and substitute therefor -- $C_{2-5}$ --;

Column 4,
Line 23, delete "$C_{2-c30}$" and substitute therefor -- $C_{2-30}$ --;
Line 24, delete "$C_{2-c5}$" and substitute therefor -- $C_{2-5}$ --;

Column 5,
Line 58, delete "$N_2$" and substitute therefor -- $H_2$ --;

Column 7,
Line 25, delete "20" before "0.9 wt. % Sn".

Signed and Sealed this

Twenty-fifth Day of December, 2001

Attest:

Attesting Officer

JAMES E. ROGAN
Director of the United States Patent and Trademark Office